US011585816B2

(12) United States Patent
Gu et al.

(10) Patent No.: US 11,585,816 B2
(45) Date of Patent: Feb. 21, 2023

(54) AUTOMATED METHOD FOR ASSESSING CANCER RISK USING TISSUE SAMPLES, AND SYSTEM THEREFOR

(71) Applicant: Proteocyte Diagnostics Inc., Toronto (CA)

(72) Inventors: Ying Gu, Toronto (CA); Jason T. K. Hwang, Toronto (CA); Kenneth P. H. Pritzker, Toronto (CA); Ranju Ralhan, Toronto (CA); Mi Shen, Toronto (CA)

(73) Assignee: Proteocyte Diagnostics Inc., Toronto (CA)

( * ) Notice: Subject to any disclaimer, the term of this patent is extended or adjusted under 35 U.S.C. 154(b) by 530 days.

(21) Appl. No.: 16/083,663

(22) PCT Filed: Mar. 14, 2017

(86) PCT No.: PCT/CA2017/050333
§ 371 (c)(1),
(2) Date: Sep. 10, 2018

(87) PCT Pub. No.: WO2017/156627
PCT Pub. Date: Sep. 21, 2017

(65) Prior Publication Data
US 2019/0072559 A1 Mar. 7, 2019

Related U.S. Application Data

(60) Provisional application No. 62/308,132, filed on Mar. 14, 2016.

(51) Int. Cl.
*G01N 33/574* (2006.01)
*C07H 21/04* (2006.01)
(Continued)

(52) U.S. Cl.
CPC ......... *G01N 33/57484* (2013.01); *A61B 5/45* (2013.01); *C07D 209/16* (2013.01);
(Continued)

(58) Field of Classification Search
CPC ....... G01N 33/57484; G01N 33/57407; G01N 2333/4727; A61B 5/45; C07D 209/16;
(Continued)

(56) References Cited

U.S. PATENT DOCUMENTS 8,160,348 B2 * 4/2012 Pinard ................ G06K 9/00127
382/133
9,240,043 B2 * 1/2016 Christiansen .......... G16B 40/00
(Continued)

FOREIGN PATENT DOCUMENTS

CA 2 797 585 A1 11/2011
CA 2 830 501 A1 9/2012
(Continued)

OTHER PUBLICATIONS

Kaur et al., "S100A7 overexpression is a predictive marker for high risk of malignant transformation in oral dysplasia", 2014, International Journal of Cancer, 134(6): 1379-1388 (Year: 2014).*
(Continued)

*Primary Examiner* — Vu Le
*Assistant Examiner* — Julius Chai
(74) *Attorney, Agent, or Firm* — Christopher N. Hunter; Laurie Wright; Blake, Cassels & Graydon LLP (57) ABSTRACT

An automated method and system for determining the risk of developing a cancer in a subject, the method comprising preparing a tissue sample obtained from the subject for visually identifying at least one biological marker associated with the cancer, digitally scanning the prepared tissue sample, analyzing the scanned image of the tissue sample to identify regions of interest, quantifying at least one param-
(Continued)

Automated ROI selection eter associated with the marker, and executing an algorithm using the quantified parameter to calculate a risk score, wherein the risk score is representative of the risk of the individual developing the cancer.

7 Claims, 3 Drawing Sheets

(51) Int. Cl.

| | |
|---|---|
| *C07D 209/16* | (2006.01) |
| *C07D 209/24* | (2006.01) |
| *C07H 1/00* | (2006.01) |
| *C07H 19/073* | (2006.01) |
| *A61B 5/00* | (2006.01) |
| *C07H 19/10* | (2006.01) |
| *G06T 7/00* | (2017.01) |

(52) U.S. Cl.
CPC ............. *C07D 209/24* (2013.01); *C07H 1/00* (2013.01); *C07H 19/073* (2013.01); *C07H 19/10* (2013.01); *C07H 21/04* (2013.01); *G01N 33/57407* (2013.01); *G06T 7/0012* (2013.01); *G01N 2333/4727* (2013.01); *G06T 2207/30024* (2013.01); *G06T 2207/30036* (2013.01)

(58) Field of Classification Search
CPC ...... C07D 209/24; C07H 1/00; C07H 19/073; C07H 19/10; C07H 21/04; G06T 7/0012; G06T 2207/30024; G06T 2207/30036
See application file for complete search history.

(56) References Cited

U.S. PATENT DOCUMENTS

| | | | |
|---|---|---|---|
| 9,298,968 B1* | 3/2016 | Peljto | G06V 20/69 |
| 2006/0063190 A1 | 3/2006 | Fischer et al. | |
| 2014/0080138 A1* | 3/2014 | Ralhan | G01N 33/6893 435/7.1 |
| 2014/0235487 A1 | 8/2014 | McDevitt et al. | |
| 2016/0012583 A1* | 1/2016 | Cales | G06T 7/0012 382/128 |
| 2016/0289307 A1* | 10/2016 | Hernández Mígiez et al. ............. C07K 16/18 |
| 2017/0030912 A1* | 2/2017 | Burwinkel | G01N 33/57415 |
| 2017/0091937 A1* | 3/2017 | Barnes | G06K 9/6228 |
| 2017/0270666 A1* | 9/2017 | Barnes | G06T 7/12 |
| 2020/0143531 A1* | 5/2020 | Xu | G06T 7/0012 |

FOREIGN PATENT DOCUMENTS

| | | |
|---|---|---|
| CA | 2830501 A1 | 9/2012 |
| CA | 2 904 441 A1 | 9/2014 |
| CA | 2904441 A1 | 9/2014 |
| WO | 2007/059629 A1 | 5/2007 |
| WO | 2014/204638 A2 | 12/2014 |

OTHER PUBLICATIONS

Extended European Search Report, dated Jul. 2, 2019, issued in corresponding European application No. 17765612.1.
Amagasa, T., M. Yamashiro, et al. (2011). "Oral premalignant lesions: from a clinical perspective." Int J Clin Oncol 16(1): 5-14.
Hsue, S. S., W. C. Wang, et al. (2007). "Malignant transformation in 1458 patients with potentially malignant oral mucosal disorders: a follow-up study based in a Taiwanese hospital." J Oral Pathol Med 36(1): 25-29.
Kalu U. E., Ogbureke, C. B. (2012). Overview of Oral Cancer. Oral Cancer. K. U. E. Ogbureke. Janeza Trdine 9, 51000 Rijeka, Croatia, InTech: 9.
Kaur, J., A. Matta, et al. (2014). "S100A7 overexpression is a predictive marker for high risk of malignant transformation in oral dysplasia." Int J Cancer 134(6): 1379-1388.
Liu, H., X. W. Liu, et al. (2015). "P16 Methylation as an Early Predictor for Cancer Development From Oral Epithelial Dysplasia: A Double-blind Multicentre Prospective Study." EBioMedicine 2(5): 432-437.
McCullough, M. J., G. Prasad, et al. (2010). "Oral mucosal malignancy and potentially malignant lesions: an update on the epidemiology, risk factors, diagnosis and management." Aust Dent J 55 Suppl 1: 61-65.
Mehanna, H. M., T. Rattay, et al. (2009). "Treatment and follow-up of oral dysplasia—a systematic review and meta-analysis." Head Neck 31(12): 1600-1609.
Pattani, K. M., Z. Zhang, et al. (2010). "Endothelin receptor type B gene promoter hypermethylation in salivary rinses is independently associated with risk of oral cavity cancer and premalignancy." Cancer Prev Res (Phila) 3(9): 1093-1103.
Ralhan, R., L. V. Desouza, et al. (2008). "Discovery and verification of head-and-neck cancer biomarkers by differential protein expression analysis using iTRAQ labeling, multidimensional liquid chromatography, and tandem mass spectrometry." Mol Cell Proteomics 7(6): 1162-1173.
Schaaij-Visser, T. B., J. F. Bremmer, et al. (2010). "Evaluation of cornulin, keratin 4, keratin 13 expression and grade of dysplasia for predicting malignant progression of oral leukoplakia." Oral Oncol 46(2): 123-127.
Speight, P. M. (2007). "Update on oral epithelial dysplasia and progression to cancer." Head Neck Pathol 1(1): 61-66.
Tripathi, S. C., A. Matta, et al. (2010). "Nuclear S100A7 is associated with poor prognosis in head and neck cancer." PLoS One 5(8): e11939.
Warnakulasuriya, S., J. Reibel, et al. (2008). "Oral epithelial dysplasia classification systems: predictive value, utility, weaknesses and scope for improvement." J Oral Pathol Med 37(3): 127-133.
Warnakulasuriya, S., T. Kovacevic, et al. (2011). "Factors predicting malignant transformation in oral potentially malignant disorders among patients accrued over a 10-year period in South East England." J Oral Pathol Med 40(9): 677-683.
Warnakulasuriya, S. and A. Ariyawardana (2016). "Malignant transformation of oral leukoplakia: a systematic review of observational studies." J Oral Pathol Med.
Weir, J. C., W. D. Davenport, et al. (1987). "A diagnostic and epidemiologic survey of 15,783 oral lesions." J Am Dent Assoc 115(3): 439-442.
Xiao, X., L. Shi, et al. (2015). "DNA content status using brush biopsy with image cytometry correlated with staging of oral leukoplakia: a preliminary study." Oral Oncol 51(1): 59-63.
Zhang, L., C. F. Poh, et al. (2012). "Loss of heterozygosity (LOH) profiles—validated risk predictors for progression to oral cancer." Cancer Prev Res (Phila) 5(9): 1081-1089.
International Search Report and Written Opinion issued in PCT/CA2017/050333, dated Jun. 14, 2017.
Ralhan R. et al.; "Early Detection of Oral Lesions with Dysplasia at High-Risk of Cancer Development Using a Proteomic Signature Image Analysis Based StraticyteTM"; Global Oral Cancer Forum 2016 (Poster); Mar. 4, 2016; http://www.globaloralcancerforum.org/img/Poster-Ralhan.pdf.

* cited by examiner

Fig. 1: Automated ROI selection

Fig. 2: Automated labelling

Fig. 3: Overlapping ROIs

AUTOMATED METHOD FOR ASSESSING CANCER RISK USING TISSUE SAMPLES, AND SYSTEM THEREFOR

CROSS REFERENCE TO PRIOR APPLICATIONS

The present application is a National Entry of PCT Application Number PCT/CA2017/050333, filed on Mar. 14, 2017, which claims priority under the Paris Convention from U.S. application Ser. No. 62/308,182, filed Mar. 14, 2016, the entire contents of which are incorporated herein by reference. The entire contents of the aforementioned applications are incorporated herein by reference.

FIELD OF THE DESCRIPTION

The present description relates generally to methods of assessing tissue samples for the risk of developing cancer. More particularly, the description relates to computer-based and/or automated methods for conducting cancer risk assessments.

BACKGROUND

Despite being a low-prevalence cancer, the 5-year mortality rate of oral cancer remains around 40% in the US and around 50% in the world. The main reason for this high mortality rate is that oral cancers are typically not diagnosed until the cancer reaches advanced stages. Most patients (67-77%) do not seek medical attention until exhibiting symptoms of persistent pain associated with advanced stage cancer. Late stage cancers are very costly and difficult to treat. In the US, the cost for the first year treatment of oral cancer is on average $79k. Diagnosis at early stages can significantly lower the mortality rate and reduce treatment costs According to the current model of oral cancer development, the cancer is believed to go through a step-wise transformation from normal to pre-malignant to invasive carcinoma (Kalu et al., 2012). However, multiple pathways may also be involved, depending on the individual, the carcinogen and possibly other factors. The fact that most early stage cancers and pre-cancers are asymptomatic makes detection of such conditions difficult for clinicians. On the other hand, oral pre-malignant lesions (or oral potentially malignant lesions) are quite common, occurring in around 2.5% of the population (Weir, et al. 1987; McCullough, et al., 2010). It would be ideal if clinicians are able to identify cancer-prone lesions before these asymptomatic lesions become cancer. To further complicate things, the progression rate (i.e. the rate of lesions becoming cancers) is very low, below 5% per year (Hsue et al., 2007; Mehanna et al., 2009). The high mortality rate of oral cancer and the low transformation rate of pre-malignant lesions create a strong demand for a method or system that can reliably detect cancer-prone lesions. Unfortunately, till now such a reliable diagnostic method or system has not been available.

Currently, there is no prognostic tool for oral pre-malignant lesions other than histopathological assessment which is in itself problematic. First, the predictive value of histopathological grading of pre-malignant lesions is very low. Generally, dysplastic lesions of higher grades have higher progression probability but have wide ranges. "A maximum of 50% of severe dysplasias, 30% of moderate dysplasias and very few (<5%) mild dysplasia are thought to progress to cancer" (Speight 2007). Thus, such grading is insufficient to provide clinicians with clear guidance on how to treat each individual pre-malignant oral lesion. Second, there is great inter- and intra-observer variation on grading. Histopathological assessment by pathologists requires specialty experience, namely, oral pathology training. Pathologists experienced in grading other tissue biopsies are not necessarily competent in grading oral lesions. Variations in an individual's experience, combined with a lack of consensus on the features to complete the evaluation, has contributed to great inter- and intra-observer variation (Warnakulasuriya et al. 2008). As a result of this subjectivity, the same lesion may receive different diagnoses or treatments depending on which clinician assesses the lesion. The end result is that in clinics, clinicians have considerably difficulty in applying the grading to treatment options. Thus, in view of the low progression rate of a lesions, clinicians typically elect simply to monitor the lesion instead of taking pre-emptive measures. Consequently, most high-risk pre-malignant lesions are not diagnosed, treated or otherwise addresses, resulting in at least some of these lesions eventually transforming to cancer.

Considerable efforts have been made to develop clinical and/or biomarker tests to enhance the prognostic range and to identify high-risk lesions. There is general consensus that high histopathological grading and advanced age are associated with high risk of progression to cancer (Schaaij-Visser, et al. 2010; Amagasa et al. 2011; Warnakulasuriya et al., 2011). In some cases, controversies regarding gender have arisen (Amagasa et al. 2011; Warnakulasuriya et al., 2015). A number of biomarkers have been proposed for association with oral lesion risk, including but not limited to hypermethylation of endothelin receptor type B (EDNRB) and kinesin family member 1A (KIF1A) (Pattani et al., 2010), loss of heterozygosity (Zhang et al., 2012), p16 methylation/HPV (Liu et al., 2015), DNA content (Xiao et al., 2015), and S100A7 (Kaur, R. et al., 2014). However, none of these markers has yet been used commercially. Moreover, there is no quantitative method to predict the progression rate in individual dysplasia.

US 2014/0235487 provides a quantitative method for determining the risk of developing oral cancers wherein certain morphological data of individual cells are used to calculate a risk score.

There exists a need for a method, and system, that can provide a reliable means of determining the risk of a subject developing cancer, such as head and neck or oral cancer.

SUMMARY OF THE DESCRIPTION

In general, described herein is a method of automatically quantifying a risk score representative of the risk that a subject, or individual, will develop a cancer. The method is based on a tissue sample obtained from the subject and prepared to visually identify at least one biological marker. The preparation may involve, for example, staining. The prepared sample is then analyzed by a visualization system and the results of such system are processed according to an algorithm, which calculates the risk score.

In one aspect, there is provided a method of prognosing the risk of developing a cancer in a subject, the method comprising:
preparing a tissue sample obtained from the subject for visually identifying at least one biological marker associated with the cancer;
digitally scanning the prepared tissue sample with a digital scanner to generate a scanned image of the sample;

analyzing the scanned image with an image analyzer to identify at least one region of interest and to quantify at least one parameter that characterizes the presence of the at least one biological marker;

transmitting the at least one quantified parameter to a processor, the processor being programmed to execute an algorithm for determining a risk score representative of the risk of the individual developing the cancer based on the at least one quantified parameter; and, executing the algorithm to generate the risk score.

In another aspect, there is provided a system for prognosing the risk of developing a cancer in a subject, the system comprising:

a scanning module for digitally scanning a biological sample obtained from the subject and generating a scanned image of the sample, the sample being pretreated to visually identify at least one biological marker associated with the cancer;

a visualization module for analyzing the scanned image to identify at least one region of interest and to quantify at least one parameter that characterizes the presence of the at least one biological marker; and, a processor programmed to execute an algorithm for determining a risk score representative of the risk of the individual developing the cancer based on the at least quantified parameter.

BRIEF DESCRIPTION OF THE FIGURES

The features of certain embodiments will become more apparent in the following detailed description in which reference is made to the appended figures wherein.

DETAILED DESCRIPTION

The terms "comprise", "comprises", "comprised" or "comprising" may be used in the present description. As used herein (including the specification and/or the claims), these terms are to be interpreted as specifying the presence of the stated features, integers, steps or components, but not as precluding the presence of one or more other feature, integer, step, component or a group thereof as would be apparent to persons having ordinary skill in the relevant art.

As discussed above, oral pre-malignant lesions (OPLs) are quite common, frequently asymptomatic, and generally detected during routine oral exams. While the transformation rate of pre-cancerous lesions to cancerous lesions is less than 5% per year, most early stage cancers and OPLs are also asymptomatic, making identification more difficult. Most OPLs do not require aggressive treatment; however, preventing the transformation to malignancy is key to impacting oral cancer morbidity and mortality. Furthermore, the high mortality rate associated with oral cancer and the low transformation rate of OPLs creates a need for reliable assessments that more accurately identify lesions at high-risk of transformation, separating these lesions from those at lesser transformation risk. The standard of care for OPL risk assessment, namely, dysplasia grading by histopathology, is subject to intra- and inter-observer variation as well as significant overlap between grades, thereby rendering such known method unreliable as a prognostic tool. The method and system described herein has been developed as a prognostic tool to meet these needs.

The present description relates to a method, in particular an automated method, of determining a subject's (i.e. patient's) risk of developing a cancer. In one aspect, the description involves conducting an automated image analysis of a tissue sample that has been stained for one or more biological markers associated with the cancer. Such markers may be cell morphologic properties (such as protein or nucleic acid markers for example. Preferably, the one or more biological markers are one or more protein biomarkers. The cancer in question may be any cancer to which the biological marker has been correlated. The correlation may be a reduction or increase in the amount or concentration of the marker when the cancer is present.

As mentioned above, a preferred biological marker is one or more protein markers. In such case, the image analysis would involve treating a biological sample obtained from the subject with an agent for visually detecting the presence or absence of the protein marker. In one example, the means of visually detecting the presence of a given protein involves the use of 3,3'-diaminobenzidine (or "DAB"). In such case, the sample obtained from the subject is contacted with an antibody specific to at least one of the protein markers under investigation, the antibody being conjugated with a peroxidase enzyme. Once the antibody is allowed to bind to the protein(s) of interest, the sample is treated with hydrogen peroxide and DAB. The DAB is thereby oxidized, forming a brown precipitate. The brown precipitate can then be visually detected and the presence and intensity of such color enables the detection of the protein(s). It will be understood that this specific visualization technique is only one example of the types of marker detection methodologies that would be known to persons skilled in the art.

According to the described method, once a particular visualization technique has been chosen and the necessary reagents deployed on the patient sample, the stained sample is then analyzed by an automated system. One such analytical visualization system is commercially available from Visiopharm™, which is discussed further below. However, it will be understood that the present description is not limited to any particular visual detection system, apparatus or method. Indeed, any system, apparatus or method that is capable of detecting stained samples and generating analytical data may be used in accordance with the present description.

The visualization system first identifies a region of interest (ROI) within the sample. The ROI is preferably identified or delineated based on the detected concentration of the marker(s) in question in the tissue as well as the location of the marker(s) in the tissue. Such location information would preferably also include topologic location information concerning the location of the marker(s) within the tissue. For example, the information may indicate the amount of the marker(s) in the epithelium This detection may involve a "heat map" methodology, wherein the intensity of a stain color (e.g. brown, in the case of DAB) indicates concentration of the marker. The ROI determination would preferably require a threshold intensity to be determined initially. Once the threshold intensity is set, the visualization system would automatically identify the ROI. Such ROI may be visually represented by one or more boundary lines to identify areas of marker concentration that exceed the concentration threshold. These regions, or "hot spots", superimposed on a digital image of the sample.

After this, the visualization system then conducts a further data acquisition step on the ROIs that are identified. In this step, the system calculates the value of at least one parameter representative of the presence of the biological marker. In one aspect, the visualization system calculates the values of at least two parameters, namely: (1) a first parameter, P1, comprising for example a value representing the percentage of the ROI area that is positive for the marker(s) in question; and (2) a second parameter, P2, comprising for example a value representing the average cell size of the cells within the ROI. As will be understood, this step can be conducted automatically using software associated with the visualization system. It will be understood that in other embodiments, further parameters may be determined either quantitatively or qualitatively. For example, in one embodiment, the presence of the marker(s) in question may be determined at the subcellular level, thus providing data on the sub-cellular localization of the marker(s) within the cells in the ROI. It will be understood that the description is not limited to the number of other parameters that may be incorporated into the analysis.

Once the values of at least the two parameters, P1 and P2, are calculated, the visualization system transmits such data to a processor for further processing. The processor may be part of or otherwise associated with the same hardware system used to conduct the visualization procedure or it may be associated with a separate hardware component such as a local or remote computer or server. The processor is programmed to receive the values of P1 and P2 to perform one or more further mathematical operations on same. In particular, the processor of the present description is encoded to execute a first algorithm to calculate a risk score, RS. The risk score is calculated by multiplying each of the parameters, P1 and P2, with a suitable weighting factor and then subtracting the weighted average cell size value from the weighted marker-positive area value. In other words, the following function is executed:

$$RS=(w_1 \times P1)-(w_2 \times P2)$$

wherein, $w_1$ is the weighting factor (or weight) for P1 and $w_2$ is the weighting factor for P2. It will be understood that the weighting factors can vary based on the marker or markers in question and on the desired sensitivity of the analysis. The values for the weighting factors can be calculated using any statistical modelling techniques or methods as would be known in the art. For example, the calculation of the weighting factors may involve linear regression or Cox regression methods based on a given data set. In the Example contained herein, weighting factors (i.e. $w_1$ and $w_2$) were calculated in the context of assessing the risk of developing oral cancer based on the protein S100A7 as the cancer marker. These weighing factors were calculated using a multivariate Cox regression model based on the test samples mentioned in the Example. The description is not limited to any particular method or methods for calculating weighting factors.

The processor is also programmed to calculate a probability value, PV, that the cancer will develop within a time period t. The equations used to calculate PV are as follows:

$$PV=1-S(t)$$

$$S(t)=\exp(-H(t))$$

$$H(t)=\int_0^t h_0(u)\exp(RS)d(u)$$

In the above equations:
PV is, as indicated above, the probability of developing cancer within a time period t.
S(t) is the probability of not developing cancer within the time period t.
H(t) is the cumulative baseline hazard up to time t.
Further description of these equations is provided below in relation to an example for illustration purposes.

As described above, the system for performing the visualization of the sample need not necessarily be physically located together with the processor that conducts the aforementioned risk calculations. Thus, in one aspect, the visualization procedure can be performed at a lab located in one location. The results, i.e. quantified parameters P1 and P2, can then be transferred or transmitted to another location where the processor may be situated, which processor can the execute the subsequent calculations. In this way, the processor calculating the risk value(s) may be located a separate office, such as an office of a data analysis service provider. The service provider can then provide a clinician or physician or patient with the calculated risk value. The above description has involved two entities, the lab and the service provider. However, it will be understood that any number (i.e. one or more entities) may be involved in the data analysis/manipulation process.

As described in the example below, the above automated method was used to determine the risk of developing oral cancer in patients, wherein the protein marker S100A7 was utilized. This marker has been described as a known biomarker for head and neck cancer (Ralhan et al., 2008; Tripathi et al., 2010) and later for oral mucosal dysplasia (Kaur et al. 2014). It is believed that the method presented herein is the first to quantitatively determine a risk for developing oral cancer in oral pre-malignant lesions using the marker S100A7. In addition, in view of the significant findings from the use of the present method, it is believed that it can be used in determining the development risk, in other words prognosis, of other cancers. It will be understood that the choice of biological markers will depend on the cancer under review.

As will be understood, each of the steps of preparing the tissue sample, scanning the tissue sample, analyzing the scanned image and processing the quantified parameter(s) can be performed at discrete locations or in the same location as needed. Further any group or subset of the steps can be performed at the same location or at different locations. In either case, it will be understood that the data generated by each step can be transmitted in any manner as would be commonly known. For example, the data from one step can be passed to the other step over any data communication network, or may be physically transported from one location to another by means of a memory device, such as a USB device, disk etc. The present description is not limited by the means by which data is transmitted.

As would be understood, the description also encompasses a system for performing the aforementioned method steps. Such a system would include a digital scanning system or device (also referred to herein as a scanning module, which would be understood to encompass hardware and associated software), that is capable of scanning a biological sample that has been treated to visually identify one or more biological markers. The system would also include an image analysis system, or visualization system (also referred to herein as a visualization module, which would be understood to encompass hardware and associated software), for analyzing the digital image generated by the scanning system. The visualization system may, for example, identify the regions of interest in the scanned image and also generate one or more quantified parameters representative of the presence and concentration etc. of the marker. The system described herein would preferably also include a processor for receiving the quantified parameter(s) and for executing an algorithm that calculates a risk score based on the value(s) of the parameter(s). The risk score would be representative of the risk to the subject of developing the cancer.

The present description will now be illustrated by means of the following example. It will be understood that the example is not meant to limit the scope of the description in any way.

Example

Summary

Oral pre-malignant lesion (OPL) biopsy samples from 150 cases with a follow-up history of up to 12 years were used. Immunohistochemistry for the biomarker S100A7 on tissue biopsy slides and tissue microarrays were performed at Mount Sinai Hospital in Toronto, Ontario, Canada. The slides were then digitally scanned on a slide scanner and images were visualized and analyzed using Visiopharm™ VIS.

All statistical analyses and model building were conducted using the R package (version 3). Stepwise Cox Regression was used to select the parameters. A multivariate Cox Regression model was fitted to selected parameters and the C-index was used to assess the model. Estimated Log Relative-Hazards from the Cox model were referred to as risk scores and used in the cut-off selection stage to classify all cases into three risk groups: low, intermediate, and high. The Nelson-Aalen-Breslow estimate, used to calculate the baseline cancer-free survival curve, was combined with the calculated risk score to produce the expected cancer-free survival probability for each case. The Aalen-Link-Tsiatis estimate, used to estimate the variance of expected cancer-free survival probability, provided the 95% confidence interval (CI) of the cancer-free survival curve.

From the 150 cases, the 95% CI of mild, moderate, and severe dysplasia grades based on histopathological assessment, overlapped extensively throughout the first 60 months, indicating ineffective differentiation. In contrast, the 95% CIs of the groups classified according to the presently described method had minimal overlaps at month 60, achieving better differentiation. The performance of present method was evaluated by an internal validation study using the split-sample technique. Comparing the C-index (time-to-event response) and Area Under the Curve (AUC; binary response), the risk scores calculated by the present method were found to be more objective and discriminatory than histopathological dysplasia grading. Furthermore, the present method was found to outperform histopathological dysplasia grading in two clinical indices. The sensitivity between the low-risk vs. non-low-risk using the present method was 96% compared to the mild vs. non-mild dysplasia grading which was 75%, with a negative predictive value of 80% and 59%, respectively.

The present method is believed to better categorize a patient's 5-year risk of OPLs progressing to cancer. The method can be easily incorporated into clinical practice as no additional tissue samples are needed for the assessment.

Materials and Methods

Tissue Biopsy Slides 150 samples were used in this application. The tissue biopsy slides, tissue microarrays and immunohistochemistry staining have been described previously (Kaur, Sawhney et al. 2013). The staining was performed at a commercial clinical lab accredited in the province of Ontario, Canada. The slides were then digitally scanned on a Hamamatsu Nanozoomer-XR™ slide scanner. The images of the slides were visualized using Visiopharm™ VIS software (version 5.0.1.1122, Hoersholm, Denmark). Clinical information for each sample such as dysplasia grading, gender, age, etc. was provided by Mount Sinai Hospital. This project including the informed consent form was approved by Mount Sinai Hospital Research Ethics Board (project 13-0197-E).

Visiopharm™ APPs for automated regions of interest identification, cell classification, and counting The ROI selection, cell classification, and counting were performed using Visiopharm VIS. Five independent Visiopharm™ APPs were used in tandem to carry out the process.

APP1: Whole Tissue selection. The tissue on a slide was outlined for further analysis. Glass with no tissue or with staining debris was excluded.

APP2: Whole Tissue to DAB Area conversion. DAB (3,3'-diaminobenzidine) positive regions (intensity below a user-defined threshold) on the tissue were selected.

APP3: DAB Area to cell classification. Cell nuclei were labeled in the DAB positive regions.

Figure 1:
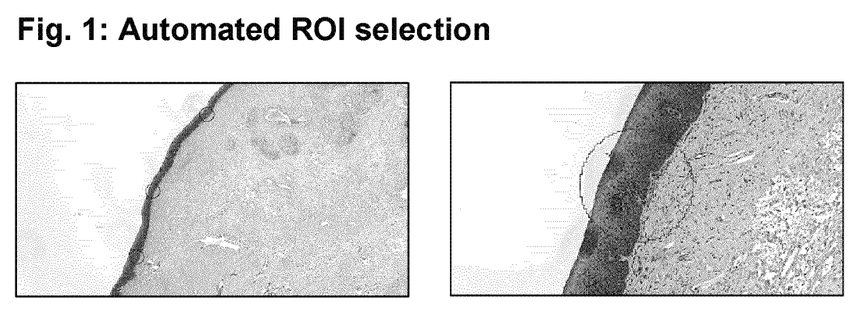
FIG. 1 illustrates the automated region of interest (ROI) selection.
Figure 3:
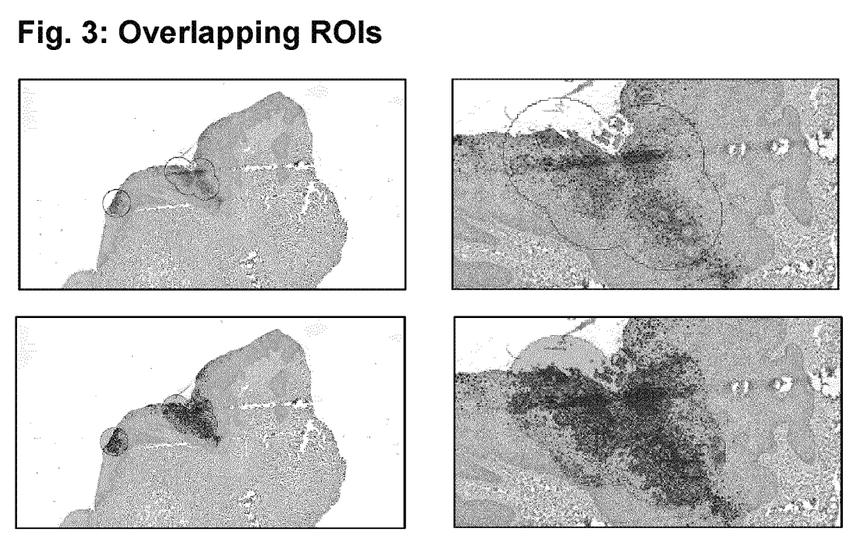
FIG. 3 illustrates an example of overlapping ROIs.

APP4: DAB Heat mapping. A heat map was generated throughout the DAB positive region based on the density of nuclei (density was defined as number of nuclei per 10 μm diameter circle). Five hottest spots (with highest density of nuclei) were selected and five 500 μm diameter circles were created the centers at each of the hot spot. These circles might overlap, giving irregular shapes (FIGS. 1 and 3).

Figure 2:
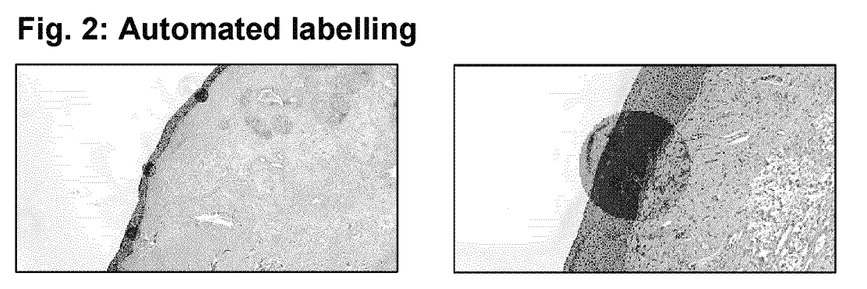
FIG. 2 illustrates the automated labelling of the ROI.

APP5: Nuclei classification and Positive DAB % calculation. Only tissue found inside the regions of interest (ROIs) as determined in APP4 were included at this stage. Areas void of tissue (background) was designed to be absent from any analysis. The nuclei were re-labeled which not necessarily overlapped with the labels in APP3. Cytoplasm were classified and labeled as either positive or negative for DAB staining. Data on two parameters were recorded, the average size of cells and the percentage of DAB positive areas versus the total area of ROIs (FIG. 2).

Algorithm

The present algorithm has two major steps. The first step, "image analysis", is used to obtain measurements of S100A7 from slide images. The second step, "risk calculation", is used to feed the measurements from the first step to a formula to produce cancer progression probability. These two steps are discussed further below.

1) Image Analysis.

Figure 4A:
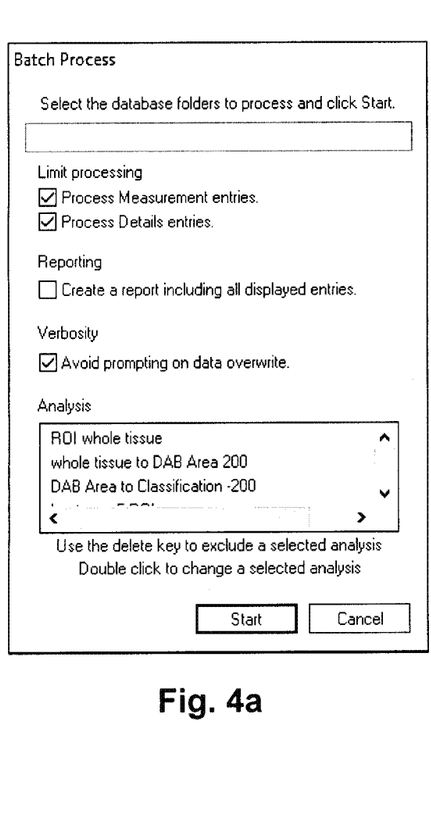
FIGS. 4a and 4b illustrate examples of input screens from the Visiopharm™ software used for the image analysis in the example.
Figure 4B:
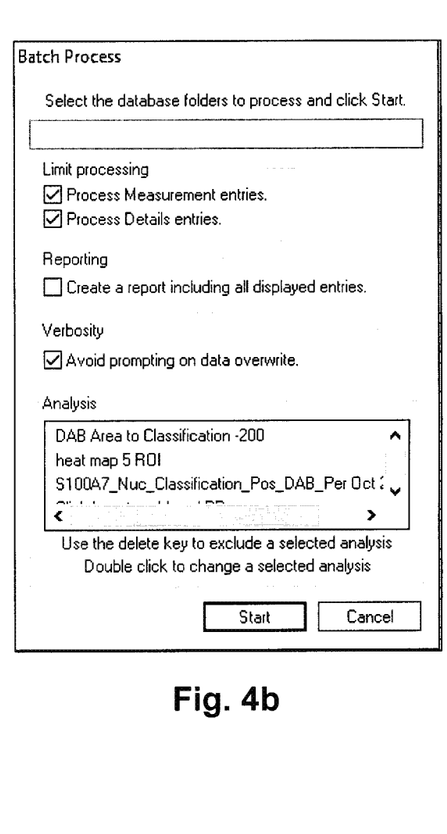

In Visiopharm™, first "batch process" is selected. Five applications, or APPs, are added sequentially into the Batch process window and the APPs are executed. FIGS. 4a and 4b illustrate sample input screens for selecting the desired APPs.

2) Risk Calculation.

The calculation takes values DAB_Pos_Per and Average_cell_size and inputs into the following formula to provide the cancer progression risk over the next five years:

$$\text{Risk Score} = [2.9807 \times (DAB\_Pos\_Per)] - [0.005636 \times (\text{Average\_cell\_size})]$$

In the above formula, DAB_Pos_Per represents the percentage of DAB positive area within the region of interest (ROI) and Average_Cell_Size represents the average size of the cells (both DAB positives and negatives) within the ROI.

3) Cancer Progression Risk Calculation.

Probability of Cancer before time $t = 1 - S(t)$

Where S(t) is the probability of not having cancer before time t, given by the following formula:

$$S(t) = \exp(-H(t))$$

Where H(t) is the cumulative baseline hazard up to time t, given by the following formula:

$$H(t) = \int_0^t h_o(u) \exp(2.9807 * DAB\_Pos\_Per - 0.005636 * Average\_cell\_size) d(u)$$

In the above formula, $h_0(t)$ is the baseline hazard, depends on the time point t.

Statistical Analysis and Modeling

All statistical analyses and model building were conducted using R package (version 3.2.2). Stepwise Cox regression was used to select parameters. A multivariate Cox regression model was fitted to the selected parameters and C-index was used to assess the model. Estimated log relative-hazards from the Cox model were referred as risk scores and were used in the cut-off selection stage to classify all cases into three risk groups. Statistical analysis was based on 150 cases and parameters based on automatically outlined ROIs. Cox-regression was used to develop risk score formula.

Results

Table 1 summarises the results of the 150 cases that were reviewed in this study.

TABLE 1

|  |  | Total | Dysplasia grading | | |
|---|---|---|---|---|---|
|  |  |  | Mild | Moderate | Severe |
| n |  | 150 | 65 | 54 | 31 |
| Cancer (% of cancer cases) |  | 60 (40.0%) | 14 (21.5%) | 24 (44.4%) | 22 (71.0%) |
| Gender | Male | 76 | 32 | 27 | 17 |
|  | Female | 74 | 33 | 27 | 14 |
| Site | Tongue | 99 | 46 | 39 | 14 |
|  | Others | 51 | 19 | 15 | 17 |
| Age (year) | mean | 59 | 59 | 60 | 60 |
|  | median | 60 | 60 | 62 | 58 |
|  | range | [32, 88] | [33, 88] | [37, 88] | [32, 83] |
| DAB_Pos_Per | mean | 47 | 40 | 48 | 57 |
|  | median | 50 | 42 | 48 | 66 |
|  | range | [1, 93] | [1, 87] | [1, 92] | [2, 93] |
| Average cell size | mean | 163 | 183 | 147 | 150 |
|  | median | 150 | 164 | 143 | 136 |
|  | range | [75, 492] | [87, 492] | [75, 242] | [79, 261] |

Classification of Dysplasia Cases into Three Risk Groups

A common difficulty with dysplasia grading is that the three grades are not good predictors of cancer progression with extensive overlap between the mild, moderate and severe groups. With the risk scores developed, two cut-offs were selected to classify all cases into 3 risk groups: low risk, intermediate risk and high risk.

1. For all patients: choose a high cut-off to differentiate high risk group and non-high (intermediate and low) risk group
    a) Specificity>85%
    b) P value of Log Rank test between high risk group and non-high risk group<0.05
    c) Among cut-offs that meet the first two criteria, choose the one that gives the best balanced accuracy, defined as the average of sensitivity and specificity
2. For patients in non-high risk group: choose a low cut-off to differentiate intermediate risk group and low risk group
    a) Sensitivity>90%
    b) P value of Log Rank test between intermediate risk group and low risk group<0.05
    c) Among cut-offs that meet the first two criteria, choose the one that gives the best balanced accuracy Table 2 summarizes the risk group cut-offs.

TABLE 2

| Cancer progression probability in 5 years | Risk group |
|---|---|
| probability ≥ 60% | High risk |
| 19% ≤ probability < 60% | Intermediate risk |
| probability < 19% | Low risk |

The algorithm used in the present example was found to classify dysplasia more accurately than histopathological grading in relation to cancer progression.

Once the 5-year cancer progression probability is calculated, a patient can be classified into one of three risk groups. The Nelson-Aalen-Breslow estimate was used to calculate the baseline cancer free survival curve. Based on risk score and the baseline cancer free survival curve, the expected cancer free survival probability for a patient can be calculated.

The Aalen-Link-Tsiatis estimate was used to estimate the variance of expected cancer free survival probability. Based on the variance and expected cancer free survival probability, the 95% confidence interval (CI) of the cancer free survival curve is generated. A log-log transformation is used when generating CIs so that the CIs are bound by [0%, 100%]. The 5-year expected cumulative cancer progression probability curve is then plotted as 100%−cancer free survival probability (%), with 95% CI calculated as [100%-95% CI of cancer free survival probability upper bound, 100%-95% CI of cancer free survival probability lower bound].

Figure 5A:
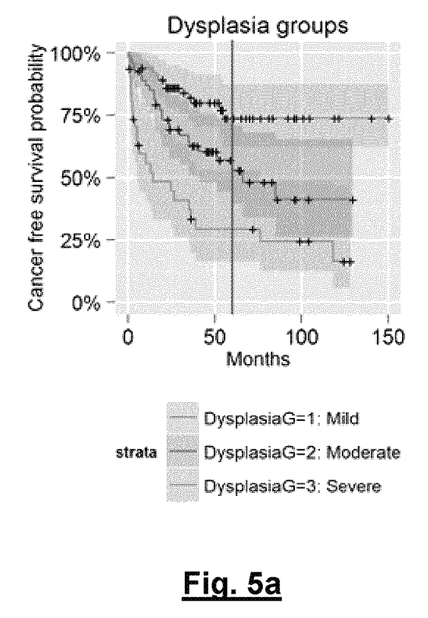
FIGS. 5a and 5b shows the Kaplan-Meier survival curves for the two groups of cases studied in the example.
Figure 5B:
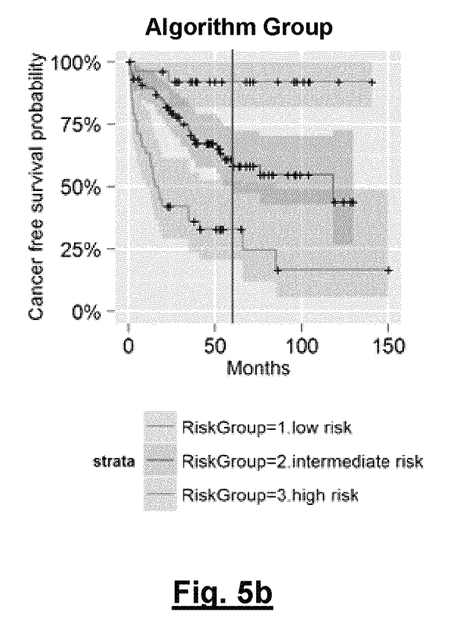

Using the 150 cases, the 95% CIs of risk categories based on histopathological assessment overlapped extensively throughout the first 60 months, indicating inefficient differentiation. In contrast, 95% CIs of the test groups had minimal overlapping at month 60, thus achieving better differentiation. FIGS. 5a and 5b illustrate the Kaplan-Meier survival curves for the two groups.

Performance of Algorithm

The performance of the algorithm was evaluated by an internal validation study using split-sample technique. In the validation study, the data set with 150 cases was randomly split into two data sets: a training set with 110 cases and a testing set with 40 cases. The algorithms (both Cox regression model and cut-off selection steps) were rebuilt from scratch using the training set. The cases in the testing set were classified using the rebuilt algorithm into three risk groups. This procedure was repeated 100 times. C-index (using time-to-event response) and AUC (using binary response) of the risk scores were recorded for each testing set.

As shown in Table 3, the calculations of the C-index and AUC indicate that the risk scores based on the algorithm were more objective and discriminatory than the known dysplasia grading method.

TABLE 3

| Predictor | C-index | AUC |
| --- | --- | --- |
| Dysplasia grading (mild, moderate, severe) | 0.67 | 0.67 |
| Algorithm risk score | 0.72 | 0.72 |

Clinical Performance

As illustrated in Tables 4 and 5, some of the improvements offered by the present algorithm-based method over the known dysplasia grading method are:

1) Higher sensitivity in the low cut-off, 92% (vs 74%), a 25% improvement.

2) Reduced false negative rate, 8% (vs 26%), by more than two-thirds.

3) Reduced false omission rate 24% (vs 39%), by almost two-fold.

TABLE 4

Dysplasia grading results

| | Dysplasia grading | | | |
| --- | --- | --- | --- | --- |
| | Sensitivity | Specificity | PPV | NPV |
| Severe vs Moderate + Mild | 37% | 83% | 76% | 48% |
| Severe + Moderate vs Mild | 75% | 53% | 69% | 59% |

TABLE 5

Results from algorithm

| | Straticyte | | | |
| --- | --- | --- | --- | --- |
| | Sensitivity | Specificity | PPV | NPV |
| High vs Intermediate + Low | 42% | 85% | 80% | 51% |
| High + Intermediate vs Low | 96% | 24% | 64% | 80% |

Although the above description includes reference to certain specific embodiments, various modifications thereof will be apparent to those skilled in the art. Any examples provided herein are included solely for the purpose of illustration and are not intended to be limiting in any way. Any drawings provided herein are solely for the purpose of illustrating various aspects of the description and are not intended to be drawn to scale or to be limiting in any way. The scope of the claims appended hereto should not be limited by the preferred embodiments set forth in the above description, but should be given the broadest interpretation consistent with the present specification as a whole. The disclosures of all prior art recited herein are incorporated herein by reference in their entirety.

References

Amagasa, T., M. Yamashiro, et al. (2011). "Oral premalignant lesions: from a clinical perspective." Int J Clin Oncol 16(1): 5-14.

Hsue, S. S., W. C. Wang, et al. (2007). "Malignant transformation in 1458 patients with potentially malignant oral mucosal disorders: a follow-up study based in a Taiwanese hospital." J Oral Pathol Med 36(1): 25-29.

Kalu U. E., Ogbureke, C. B. (2012). Overview of Oral Cancer. Oral Cancer. K. U. E. Ogbureke. Janeza Trdine 9, 51000 Rijeka, Croatia, InTech: 9.

Kaur, J., A. Matta, et al. (2014). "S100A7 overexpression is a predictive marker for high risk of malignant transformation in oral dysplasia." Int J Cancer 134(6): 1379-1388.

Liu, H., X. W. Liu, et al. (2015). "P16 Methylation as an Early Predictor for Cancer Development From Oral Epithelial Dysplasia: A Double-blind Multicentre Prospective Study." EBioMedicine 2(5): 432-437.

McCullough, M. J., G. Prasad, et al. (2010). "Oral mucosal malignancy and potentially malignant lesions: an update on the epidemiology, risk factors, diagnosis and management." Aust Dent J 55 Suppl 1: 61-65.

Mehanna, H. M., T. Rattay, et al. (2009). "Treatment and follow-up of oral dysplasia—a systematic review and meta-analysis." Head Neck 31(12): 1600-1609.

Pattani, K. M., Z. Zhang, et al. (2010). "Endothelin receptor type B gene promoter hypermethylation in salivary rinses is independently associated with risk of oral cavity cancer and premalignancy." Cancer Prev Res (Phila) 3(9): 1093-1103.

Ralhan, R., L. V. Desouza, et al. (2008). "Discovery and verification of head-and-neck cancer biomarkers by differential protein expression analysis using iTRAQ labeling, multidimensional liquid chromatography, and tandem mass spectrometry." Mol Cell Proteomics 7(6): 1162-1173.

Schaaij-Visser, T. B., J. F. Bremmer, et al. (2010). "Evaluation of cornulin, keratin 4, keratin 13 expression and grade of dysplasia for predicting malignant progression of oral leukoplakia." Oral Oncol 46(2): 123-127.

Speight, P. M. (2007). "Update on oral epithelial dysplasia and progression to cancer." Head Neck Pathol 1(1): 61-66.

Tripathi, S. C., A. Matta, et al. (2010). "Nuclear S100A7 is associated with poor prognosis in head and neck cancer." PLoS One 5(8): e11939.

Warnakulasuriya, S., J. Reibel, et al. (2008). "Oral epithelial dysplasia classification systems: predictive value, utility, weaknesses and scope for improvement." J Oral Pathol Med 37(3): 127-133.

Warnakulasuriya, S., T. Kovacevic, et al. (2011). "Factors predicting malignant transformation in oral potentially malignant disorders among patients accrued over a 10-year period in South East England." J Oral Pathol Med 40(9): 677-683.

Warnakulasuriya, S. and A. Ariyawardana (2015). "Malignant transformation of oral leukoplakia: a systematic review of observational studies." J Oral Pathol Med.

Weir, J. C., W. D. Davenport, et al. (1987). "A diagnostic and epidemiologic survey of 15,783 oral lesions." J Am Dent Assoc 115(3): 439-442.

Xiao, X., L. Shi, et al. (2015). "DNA content status using brush biopsy with image cytometry correlated with staging of oral leukoplakia: a preliminary study." Oral Oncol 51(1): 59-63.

Zhang, L., C. F. Poh, et al. (2012). "Loss of heterozygosity (LOH) profiles—validated risk predictors for progression to oral cancer." Cancer Prev Res (Phila) 5(9): 1081-1089.

We claim:

1. A method of prognosing the risk of developing oral cancer in a subject, the method comprising:

staining, with a stain for a biological marker comprising S100A7, a tissue sample obtained from a pre-cancerous lesion of the subject to obtain a stained tissue sample;

digitally scanning the stained tissue sample with a digital scanner to generate a scanned image of the stained tissue sample;

analyzing the scanned image with an image analyzer to generate intensity values correlated to an amount of the biological marker present in the tissue;

identifying at least one region of interest, the at least one region of interest being defined by intensity values that exceed a predetermined threshold intensity;

quantifying two parameters that characterize the presence of the biological marker;

transmitting the two quantified parameters to a processor, the processor being programmed to execute an algorithm for determining a risk score representative of the risk of the individual developing the cancer based on the two quantified parameters; and, executing the algorithm to generate the risk score;

wherein:

the step of analyzing is performed automatically following the step of scanning; and the two parameters represent (i) an area within the at least one region of interest comprising the biological marker, and (ii) an average size of the cells within the at least one region of interest; and wherein the at least one region of interest has a maximum diameter of 500 µm.

2. The method of claim 1, wherein the digital scanner, the image analyzer and the processor are connected together over a data communication network.

3. The method of claim 1, wherein the at least one region of interest is circular.

4. The method of claim 1, wherein there are five regions of interest.

5. A system for prognosing the risk of developing oral cancer in a subject, the system comprising:

at least one computing device configured to:

receive a scanned image of a biological tissue sample obtained from a pre-cancerous lesion of the subject, the scanned image being stained with a stain for a biological marker comprising S100A7;

analyze the scanned image to generate intensity values correlated to an amount of the biological marker present in the tissue sample;

identify at least one region of interest, the at least one region of interest being defined by intensity values that exceed a predetermined threshold intensity;

quantify two parameters that characterize the presence of the biological marker; and execute an algorithm for determining a risk score representative of the risk of the individual developing the cancer based on the two quantified parameters to generate the risk score, wherein the two parameters represent (i) an area within the at least one region of interest comprising the biological marker, and (ii) an average size of the cells within the at least one region of interest, and wherein the at least one region of interest has a maximum diameter of 500 µm.

6. The system of claim 5, wherein the at least one region of interest is circular.

7. The system of claim 5, wherein there are five regions of interest.

* * * * *